United States Patent [19]
Lihme et al.

[11] Patent Number: 5,770,416
[45] Date of Patent: Jun. 23, 1998

[54] PERMEABLE HOLLOW PARTICLES HAVING AN OUTER SHELL OF MECHANICALLY RIGID POROUS MATERIAL

[75] Inventors: Allan Otto Fog Lihme, Birkerød; Thorkild Christian Bøg-Hansen, Hellerup; Claus Schäfer Nielsen, Humlebæk, all of Denmark

[73] Assignee: UpFront Chromatography A/S, Copenhagen, Denmark

[21] Appl. No.: 70,847

[22] Filed: Jun. 3, 1993

Related U.S. Application Data

[63] Continuation of Ser. No. 784,394, Dec. 30, 1991, abandoned.

[30] Foreign Application Priority Data

May 26, 1989 [DK] Denmark ................................. 2597/89

[51] Int. Cl.$^6$ .............................. C12N 11/14; C12N 5/00; G01N 33/552; B01J 20/10
[52] U.S. Cl. ........................ 435/176; 435/395; 435/403; 436/524; 436/527; 502/407; 530/811
[58] Field of Search ..................................... 435/176, 182, 435/395, 403; 436/524, 527, 531; 530/811; 502/407

[56] References Cited

U.S. PATENT DOCUMENTS

| | | | |
|---|---|---|---|
| 2,797,201 | 6/1957 | Veatch et al. | 260/2.5 |
| 2,978,339 | 4/1961 | Veatch et al. | 106/40 |
| 3,030,215 | 4/1962 | Veatch et al. | 106/40 |
| 4,138,336 | 2/1979 | Mendel et al. | 210/198 |
| 4,257,799 | 3/1981 | Rosencwaig et al. | 65/21.4 |
| 4,588,540 | 5/1986 | Kiefer et al. | 264/43 |
| 4,698,317 | 10/1987 | Inoue et al. | 501/9 |
| 4,748,121 | 5/1988 | Beaver et al. | 435/176 |
| 4,937,209 | 6/1990 | Jones et al. | 435/176 |

FOREIGN PATENT DOCUMENTS

| | | |
|---|---|---|
| 43159 | 1/1982 | European Pat. Off. . |
| 154751 | 9/1985 | European Pat. Off. . |
| 320 194 A1 | 6/1989 | European Pat. Off. . |
| 320 998 A1 | 6/1989 | European Pat. Off. . |
| 2 141 398 A | 12/1984 | United Kingdom . |
| 2 151 601 B | 7/1985 | United Kingdom . |
| 2 151 602 B | 7/1985 | United Kingdom . |
| WO 86/02093 | 10/1985 | WIPO . |

OTHER PUBLICATIONS

"Fillite" by Fillite (Roncorn) Ltd., Roncorn, Cheshire, U.K.

Patrick B. Deasy, "Microencapsulation and Related Processes", Marcel Dekker, Inc., New York and Basel 1984, Table 2.1, pp. 24–25.

Barany et al., Int. J. Peptide Proteins Res. 30 (1987) pp. 705–739.

*Primary Examiner*—David M. Naff
*Attorney, Agent, or Firm*—Foley & Lardner

[57] ABSTRACT

Permeable substantially spherical hollow particles of 1–5000 μm in size are formed having an outer shell of a mechanically rigid porous material. Pores of the shell are through-going pores that connect the inside of the particles to surroundings and allow chemical species to traverse the outer shell. To prepare the particles, impermeable hollow particles are treated with an acid or base under reflux conditions to form pores. The outer shell is formed of anhydrous forms of silicon dioxide, metal silicates, metal borosilicates, metal oxides or boric oxide. Metals and metal alloys are not used in forming the outer shell. Particles containing a polymer are formed by immersing the permeable hollow particles in a solution of components that polymerize to form the polymer, allowing the solution to partially fill the particles via the pores and polymerizing the components. The permeable particles are useful as carriers in High Performance Liquid Chromatography, gel filtration, ion exchange, affinity chromatography, immunochemical procedures, solid-phase peptide or protein synthesis, immobilization of catalysts such as enzymes and noble metals and immobilization of cells or virus particles. The particles may also be used as filtration aids, adsorbents or absorbents.

21 Claims, 4 Drawing Sheets

PERMEABLE HOLLOW PARTICLES HAVING AN OUTER SHELL OF MECHANICALLY RIGID POROUS MATERIAL

This application is a continuation of application Serial No. 07/784,394, filed Dec. 30, 1991, now abandoned.

FIELD OF THE INVENTION

The present invention relates to methods for the preparation of permeable hollow particles having an outer shell of a porous material exhibiting a high degree of mechanical rigidity, with the proviso that said material is not a material selected from metallic elements and alloys thereof, and to methods for the preparation of corresponding permeable composite particles containing a second material capable of at least temporarily interacting with one or more chemical species. The invention also relates to particles prepared by such methods, and to the use of such particles in a variety of processes.

Permeable composite particles according to the invention are particularly useful in a wide variety of processes, e.g. in High Performance Liquid Chromatography (HPLC), in gel filtration, in ion-exchange and in affinity chromatography in the form of carriers for the appropriate chromatographic substrate, in immunochemical procedures in the form of solid-phase carriers for antigens, in solid-phase peptide and protein synthesis in the form of carriers for the synthesis substrate, e.g. a polymer substrate of the traditional "Merrifield" type, in catalysis in the form of carriers for immobilized enzymes and other catalysts, such as noble metals, for use in small- or large-scale chemical syntheses, and in microbiological procedures in the form of carriers for e.g. cells or virus particles. Permeable hollow particles according to the invention are advantageous, for example, in chromatographic procedures, as filtration aids, or as adsorbents or absorbents.

BACKGROUND OF THE INVENTION

Permeable particles having a high degree of mechanical rigidity of their outer shell, such that they are resistant to collapse and, substantially, to deformation when subjected to relatively high external/internal pressure differentials, are of particular value in procedures involving the use of high pressures, notably in HPLC. in which external pressures of 100 atm or more are frequently employed. There are numerous disclosures in the prior art concerning hollow, particles prepared from inorganic or organic materials; relevant disclosures include the following patents: U.S. Pat. No. 2,978,339, U.S. Pat. No. 3,030,215, U.S. Pat. No. 4,138,336 and U.S. Pat. No. 4,257,799. However, there are relatively few disclosures concerning hollow particles which, by virtue of their having through-going pores or holes in their outer shell, or for other reasons, display a significant degree of permeability towards gases and/or liquids:

U.S. Pat. No. 4,698,317 discloses inter alia hollow, microspherical cordierite glass particles having "open pores", and a method for their preparation involving spray thermal decomposition of a solution, in an aqueous organic solvent, preferably an aqueous alcohol, containing a tetraalkyl silicate, an aluminium salt, a magnesium salt and, optionally, other compounds, the water content of the solution being adjusted so as to promote "open pore" formation. Examples of the particles in question described in the latter patent specification are as follows: (a) below 30 $\mu$m in size and with 10–350 pores of diameter 0.01–6 $\mu$m, (b) below 12 $\mu$m in size and with 50–150 pores of diameter less than 2 $\mu$m, and (c) below 10 $\mu$m in size and with pores of diameter less than 2 $\mu$m.

U.S. Pat. No. 2,797,201 discloses substantially spherical, hollow particles having a "thin, strong skin", these particles being formed by thermal treatment of droplets of a solution of a film-forming material, e.g. an organic polymer such as a phenol-formaldehyde resin, in a suitable solvent, the solution optionally further containing a "blowing agent" (sometimes also referred to as a "latent gas", i.e. a substance which generates a gas at the elevated temperature of the thermal treatment or, in some cases, which itself is gaseous (such as carbon dioxide). In the absence of a blowing agent, substantially all the resulting particles sink when subjected to a flotation test in a suitable liquid medium, indicating their permeability towards the liquid medium. Upon incorporating a blowing agent, at most 3% of the resulting particles were found to sink in flotation tests. Examples of hollow particles prepared under a particular set of conditions using a water-soluble, partially polymerized phenolformaldehyde resin (known as Durez 14798) as film-forming material in the absence of a blowing agent had sizes in the range 2–20 $\mu$m. Examples of hollow particles prepared in the presence of a blowing agent had sizes in the range 2–110 $\mu$m, the exact size distribution depending on the conditions, the film-forming material, the solvent and the nature of the blowing agent.

GB 2151601 B relates to porous hollow particles, including permeable, porous hollow particles, of an inorganic material, such as Kieselguhr and/or an inorganic oxide, and to composite material comprising such particles in which there is supported a selected substance, such as a chromatographic organic gel. The porous hollow particles may be formed by coating a fugitive core material, e.g. organic resin beads or alginate spheres, with inorganic material, and then heating to remove the fugitive core material. Examples of spherical, porous hollow particles prepared by this means had diameters of from about 500 $\mu$m to about 4000 $\mu$m.

GB 2151602 B, which is related to GB 2151601 B, discloses inter alia particles closely similar to those disclosed in the last-mentioned patent, but which incorporate a magnetic material, such as ferric oxide, nickel oxide or cobalt oxide, in the inorganic shell of the particles. These particles may be prepared by a method analogous to that mentioned above in connection with the latter patent, the inorganic material used to coat the fugitive core material then incorporating a magnetic component. The disclosed examples of magnetic, porous hollow particles prepared by this means had diameters of from 700 $\mu$m to 1500 $\mu$m.

The preparation of permeable hollow particles or permeable composite particles according to the above-mentioned disclosures requires at least either (i) the use of relatively expensive, in some cases hazardous, starting materials and solvents, and the use of special equipment for the formation of droplets of a liquid medium and for thermal treatment of the droplets, as in U.S. Pat. No. 2,797,201 and U.S. Pat. No. 4,698,317, or (ii) the use of a lengthy, multi-step building-up procedure followed by a high-temperature sintering treatment, as in GB 2151601 B and GB 2151602 B. Furthermore, the above-described prior art descriptions of the preparation of predominantly permeable hollow particles or permeable composite particles disclose particles of size-range up to about 30 $\mu$m, or from about 500 $\mu$m to about 4000 $\mu$m, particles of intermediate size not being provided for.

As mentioned earlier, above, there are numerous disclosures in the prior art concerning hollow, apparently substantially impermeable particles prepared from inorganic or organic materials. In many cases the preparation of these particles employs cheap, safe, readily obtainable starting materials and is relatively straightforward; this is the case e.g. in U.S. Pat. No. 2,978,339, U.S. Pat. No. 3,030,215 and U.S. Pat. No. 4,257,799, all of which disclose hollow particles of siliceous glass material and which typically employ an aqueous solution comprising predominantly an alkali metal silicate as the basic raw material. The particles disclosed in U.S. Pat. No. 4,257,799 are hollow glass spheres having an outer diameter ranging from about 100 $\mu$m to about 500 $\mu$m, with a substantially uniform wall thickness in the range of about 0.5–20 $\mu$m. Those disclosed in U.S. Pat. No. 3,030,215 are hollow, discrete spheres of synthetic, fused, water-insoluble alkali metal silicate-based glass with diameters of from 5 $\mu$m to 5000 $\mu$m and wall thicknesses of 0.5–10% of their diameters.

A number of types of substantially impermeable, hollow micro-spheres of siliceous material are commercially available. For example, soda-lime borosilicate glass microspheres are marketed by the 3M Corporation (USA) in a variety of size fractions, such as those sold under the codes D32/4500 (size fraction $\leq$74 $\mu$m) and B46/4000. The latter two types of particles, as supplied, are stated by the manufacturer to be able to withstand pressures of ca. 4500 psi ($\equiv$ca. 306 atm) and ca. 4000 psi ($\equiv$ca. 272 atm), respectively, without collapse.

Amongst other types of spherical hollow particles which are readily available are those sold under the name "Fillite" by Fillite (Runcorn) Ltd., Runcorn, Cheshire, U.K. The latter are siliceous micro-spheres which originate as a component of fly-ash formed upon combustion, in a combustion plant, of certain types of coal. A technical brochure supplied by the Swedish agent for "Fillite" products [Nordiska Mineralprodukter AB, Malmö, Sweden] describes these particles as "aluminium silicate", and the composition by weight (calculated as oxides) of the outer shell is given as:

| | |
|---|---|
| $SiO_2$ | 55–65% |
| $Al_2O_3$ | 27–33% |
| $Fe_2O_3$ | 4% |

The melting point of the material is given as $\geq$1200° C., and the spheres are reported to contain a 30:70 (v/v) mixture of nitrogen and carbon dioxide at a total pressure of 0.2 atm, demonstrating their essential impermeability towards gases. The manufacturer describes "Fillite" spheres as non-absorbent and totally impervious to liquids, and the average ratio of the thickness of the outer shell to the external diameter is reported to be $\frac{1}{10}$. "Fillite" spheres are cheap and are available in a variety of size fractions, e.g. "Fillite 75" (5–85 $\mu$m), "Fillite 150" (<150 $\mu$m) and "Fillite SG" (5–540 $\mu$m).

In view, inter alia, of the wide range of particle sizes and particle wall thicknesses, the insolubility and inertness in a wide variety of media, and the anticipated mechanical strength or rigidity of hollow particles of the above-mentioned, latter types, it would clearly be advantageous to be able, by means of a simple, preferably inexpensive treatment, to render such particles permeable, or to improve the permeability of any such particles which may initially have some degree of permeability but which are inadequately permeable for a particular application.

SUMMARY OF THE INVENTION

In one aspect the present invention provides a method for the preparation of permeable hollow particles having an outer shell of a porous material exhibiting a high degree of mechanical rigidity, at least some of the pores of said porous material being through-going pores traversing the outer shell, the size of substantially all of the particles being within the range from 1 $\mu$m to 5000 $\mu$m, the permeability of said particles being such as to permit certain chemical species to traverse their outer shell via said through-going pores, the method comprising taking hollow particles having an outer shell of a material exhibiting a high degree of mechanical rigidity, which hollow particles optionally initially have some degree of permeability, said optional, initial degree of permeability being lower than that which is to be attained, the size of substantially all of the particles being within the range from 1 $\mu$m to 5000 $\mu$m, treating said hollow particles with one or more reagents so as to render them adequately permeable by the formation of through-going pores in said outer shell and/or, optionally, by the enlargement of optional, previously existing through-going pores in said outer shell, and, optionally, subjecting the thus-treated, permeable hollow particles to a surface treatment so as to modify the physical and/or chemical properties of the outer and, optionally, inner surface of said outer shell and, optionally, of the walls of said formed and/or enlarged through-going pores, with the proviso that said material exhibiting a high degree of mechanical rigidity is not a material selected from metallic elements and alloys thereof.

In a further aspect, the present invention also provides a method for the preparation of permeable composite particles having an outer shell of a porous first material exhibiting a high degree of mechanical rigidity, the inner surface of said outer shell defining a cavity in which is contained a second material, said second material being capable of at least temporarily interacting with one or more chemical species, said interaction being of chemical and/or physical origin, at least some of the pores of said porous first material being through-going pores traversing the outer shell, some of said through-going pores optionally being wholly or partly filled with said second material, the size of substantially all of the composite particles being within the range from 1 $\mu$m to 5000 $\mu$m, the permeability of said composite particles being such as to permit certain chemical species to come into contact with said second material contained within said cavity and, optionally, contained within said through-going pores, the method comprising the steps described above in connection with the method according to the invention for the preparation of permeable hollow particles, together with the further steps of:

introducing said second material into, or forming in situ said second material within said permeable hollow particles, and, optionally, subjecting the thus-treated, permeable composite particles to a further surface treatment so as to:

(i) modify the physical and/or chemical properties of the outer surface of said outer shell and, optionally, of the walls of said formed and/or enlarged through-going pores, and/or (ii) hinder and/or regulate release from said permeable composite particles of a second material, or of a substance which may subsequently be formed by a chemical reaction of or by the intervention (e.g. catalytic intervention) of a second material, contained within said permeable composite particles, and/or (iii) hinder and/or regulate access of a substance present outside said permeable composite particles to a second material contained within said permeable composite particles, with the proviso that said material exhibiting a high degree of mechanical rigidity is not a material selected from metallic elements and alloys thereof.

What is meant by particles being "permeable" in the context of the present invention is that certain gaseous and/or liquid phases are capable of migrating through the outer shell of the particles. In the case of liquid phases, these may be pure liquid compounds or solutions of one or more liquid or solid compounds in a solvent liquid phase. The migration of gaseous and/or liquid phases through the outer shell will normally necessitate the presence of passageways or interconnected interstices of microscopic or sub-microscopic size, which in the present context are denoted "through-going pores". Through-going pores as formed in a method according to the present invention may arise as the result of chemical reaction and/or solvent/solute (i.e. simple dissolution) interaction of one or more reagents with the outer shell material of the hollow particles in question. However, formation of through-going pores by chemical reaction is often to be preferred, since the rate of their formation, their dimensions and the number of such pores per unit surface area are expected to be easier to regulate reproducibly than is the case for simple dissolution processes; this regulation may be achieved, for example, by varying the concentrations of the reagents employed, the temperature at which the treatment takes place and the duration of the treatment.

Clearly, the intimate details of the process by which through-going pore formation takes place will depend upon the nature as well as the degree of chemical and physical homogeneity of the material constituting the outer shell of the particles. In cases in which the outer shell material consists of a chemically and physically homogeneous, compact, solid material, attack of the material by a chemically reactive reagent may take place at a fairly uniform rate and may be such that essentially conically funnel-shaped craters are etched in the material until the point where the depth of each crater equals the original thickness of the outer shell at the point of attack, funnel-shaped passageways in the outer shell material thus being created. In the substantially complete absence of any microscopic foci or initiation points at which local, pointwise attack of the outer shell material may preferentially occur, it may, however, also be envisaged that essentially uniform etching or dissolution of the material may occur, leading to a gradual and essentially uniform decrease in the thickness of the outer shell until, ultimately, the outer shell becomes completely dissolved.

However, in cases in which the outer shell material is chemically and/or physically inhomogeneous, examples being a chemically substantially homogeneous material which has a grained structure and which has inter-grain interstices, or a chemically inhomogeneous material containing discrete domains or grains of different chemical substances, possibly further having inter-domain or inter-grain interstices, the attack of the material by a chemically reactive reagent may take place in a discontinuous manner leading to irregularly formed, possibly tortuous through-going pores. In cases such as those mentioned above in which the outer shell material has inter-grain or inter-domain interstices, the formation of through-going pores may comprise perforation of the regions of material forming the boundaries between neighbouring interstices; likewise, the enlargement of any previously existing through-going pores may comprise the enlargement of relatively small perforations in such latter-mentioned regions of material.

DETAILED DESCRIPTION OF THE INVENTION

Figure 1:
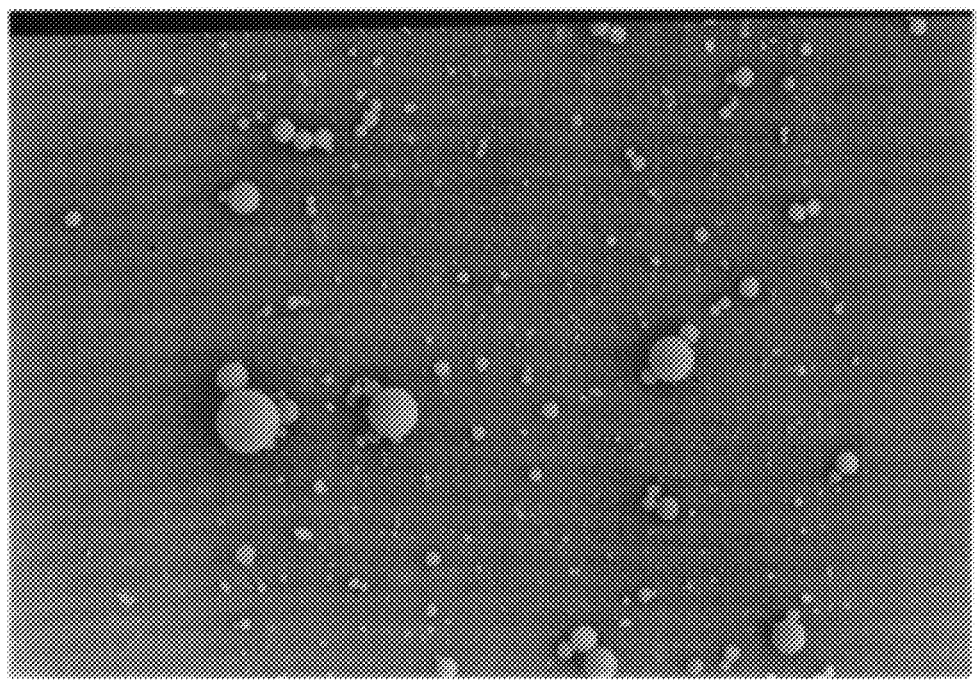
FIG. 1 (magnification ×150) shows a sample of untreated particles as supplied.

In preferred methods for the preparation of permeable hollow particles or permeable composite particles according to the present invention, the hollow particles employed are substantially impermeable prior to said treatment with said reagents. Depending on the use which is to be made of permeable hollow or permeable composite particles of the type embraced by the present invention, it may in certain cases be advantageous or essential that the outer shell material of the particles in question (optionally after one or more optional surface treatments) exhibits specificity or selectivity with respect to its affinity towards chemical species. For example, if porous hollow particles are to be used as adsorbents and/or absorbents of desired species it may be advantageous that the outer and/or inner surface of the particles and/or the walls of through-going pores of the particles exhibit specific or selective interaction with the species in question. As a further example, porous composite particles may be envisaged in which the second material, i.e. the material within the particle cavities, comprises a substance or substances which catalyze(s) a desired reaction of certain chemical species of interest. but which also catalyze(s) an undesired reaction of other chemical species that are present in the medium containing the species of interest; in such a case it will be desirable that the outer shell material shows positive affinity for the chemical species of interest and favors the migration of the species through the through-going pores, and possibly even shows negative affinity towards other species and actively disfavors their corresponding migration, so that preferential contact of the species of interest with the catalytic substance(s) is achieved. Thus, a further aspect of the invention provides methods for the preparation of permeable hollow particles or permeable composite particles in which the porous material of the outer shell is capable of at least temporarily interacting with one or more chemical species, the interaction being of chemical and/or physical origin.

Examples of chemical interaction in the present context are:

hydrogen-bonding interaction between, for example, —OH, —SH, —NHR (R being, e.g., an H atom, an alkyl group such as $CH_3$, $C_2H_5$, n-$C_3H_7$ or i-$C_3H_7$, an aralkyl group such as $CH_2C_6H_5$, or a more complex organic group), —F or —Cl groups exposed, on the one hand, on the outer and/or, optionally, inner surface of the particles and/or, optionally, on the walls of through-going pores of the particles, and, on the other hand, a relevant hydrogen-bonding group, normally one of the above-listed groups, of the interacting chemical species in question;

salt formation between an acidic group such as —$SO_3H$, —COOH or —PO($OR^1$)($OR^2$)OH ($R^1$ and/or $R^2$ being, e.g., one of the groups mentioned above in connection with an R group in —NHR) on the one hand and a basic group such as —$NH_2$ or —NHR (R being, e.g., a group as already mentioned above) on the other;

acetal or hemiacetal formation between an aldehyde group on the one hand and an alcoholic hydroxy group on the other.

Examples of physical interaction in the context of the present invention are:

dipole-dipole interaction, ion-dipole interaction and ion-ion electrostatic interaction.

By way of example, preferred embodiments of methods according to the present invention for the preparation of permeable hollow or permeable composite particles involve through-going pore formation/enlargement in siliceous hollow particles comprising silicon dioxide and, often, silicates. It is well known that the negatively charged or negatively polarized oxygen atoms of silicate groups exposed at a surface of many such siliceous materials, for example siliceous glasses, participate readily in hydrogen-bonding in the manner outlined above, either directly or in protonated form, i.e. in the form of —OH groups; thus, for example, hydroxylic substances, such as sugars and other carbohydrates, may interact relatively strongly with such siliceous materials, possibly favouring the retention to some extent of such hydroxylic substances within the cavities and/or pores of permeable particles of this type. In this connection it may also be mentioned that exposed silicate groups constitute suitable substrates for the chemical attachment of certain types of surface-treatment agents, such as organo-functional silanes, which may bring about some desired modification of the interactive or binding properties of siliceous materials.

Other types of chemical and physical interaction can be envisaged as being of relevance in the present context and are intended to be within the scope of the present invention. Furthermore, the distinction between chemical and physical interaction is in certain instances diffuse and is not, within the context of the present invention, intended to be applied in too rigid a fashion, in that certain forms of interaction, e.g. hydrogen-bonding interaction, can justifiably be argued as belonging to both categories.

An optional surface treatment or an optional further surface treatment in a method according to the invention for the preparation of permeable hollow or permeable composite particles may, for example, entail reaction of functional groups present on the outer surface and, optionally, on the walls of through-going pores of the particles with an appropriate reagent so as to reduce or prevent undesired chemical and/or physical interaction of these functional groups with a chemical species present in the medium to which the particles are to be exposed, or so as to attach a further chosen functional group or a substituent bearing such a functional group which can lead to the binding of desired substances (e.g. by ion-exchange). One example is provided by the above-mentioned reaction of silicate groups exposed at free surfaces of siliceous materials with organo-functional silanes; one such organo-functional silane which has proved useful in the case of preferred embodiments of permeable hollow particles in the context of the present invention is 3-glycidoxypropyltrimethoxysilane, the resulting particles showing, for example, reduced non-specific binding of human serum proteins relative to the untreated permeable hollow particles.

Alternatively, an optional surface treatment or an optional further surface treatment may (especially in cases where it is desired to hinder and/or regulate the release from permeable composite particles of a second material contained within the permeable composite particles, or to hinder and/or regulate the release of a product formed via the chemical reaction of or the intervention of such a second material, or to hinder and/or regulate access of a substance present outside permeable hollow particles or permeable composite particles to the interior of permeable hollow particles or to a second material contained within permeable composite particles) entail the coating of the particles in question with a suitable coating (film-forming) material; a suitable material may, for example, be a natural or synthetic organic polymeric material through which certain desired types of substances gradually diffuse or migrate, or which by other means (such as pH-dependent or enzymatic breakdown of the coating material) can regulate the diffusion or migration of the substance(s) in question into and/or out of the particles.

The nature of such a coating material will depend upon the nature of the outer shell material of the permeable particles and on the function which the coating is to perform, and examples of coating materials which may be suitable are: an acrylic polymer or copolymer. such as that known as "Eudragit E 30 D", or an cellulose derivative such as the ethylcellulose derivative known as "Aquacoat ECD-30"; the latter two examples may be applied to a surface from an aqueous dispersion. Other coating materials of relevance may be selected, for example, from those listed in: Patrick B. Deasy, *Microencapsulacion and Related Processes*, Marcel Dekker, Inc., New York and Basel 1984, Table 2.1, pp. 24–25.

The optimum dimensions of permeable hollow or permeable composite particles of the type prepared by a method according to the present invention will largely depend upon the use to which they are to be put, although limitations dictated by the nature of the outer shell material and/or, in the case of permeable composite particles, by the nature of the second material within the particles may also play a role. From the point of view of achieving the greatest rate of interaction of chemical species with a given mass of particles of a particular type, it will generally be advantageous that the total surface area of the particles en masse is as large as possible, and thus that the size of the particles is as small as possible. However, when the particles in question are to be used, for example, in column chromatographic procedures, a major factor determining the practical lower limit to the size of the particles will be the resistance to flow of the fluid medium through the close-packed particles. The normal size ranges appropriate, for example, for traditional applications of solid, particle-formed chromatographic substrates will be known to a person skilled in the art. In preferred aspects of methods for the preparation of permeable hollow particles or permeable composite particles according to the present invention, the size of substantially all of said hollow particles, and thereby of said prepared permeable hollow particles, is within the range of 1–5000 $\mu$m, suitably 1–4000 $\mu$m, advantageously 1–3000 $\mu$m, preferably 1–2000 $\mu$m, more preferably 1–1000 $\mu$m, most preferably 1–500 $\mu$m, such as 1–100 $\mu$m, including 5–85 $\mu$m.

For permeable particles within the context of the present invention to be of use, for example, in chromatographic separation processes, the time-scale of the process of migration of fluid (i.e. gaseous or liquid) phases through the outer shell of the particles. where relevant, should preferably be short in order to ensure sufficiently radid equilibration between extra and intraparticular phases; this time-scale will often be of the order of fractions of seconds. Ignoring all other considerations, this will clearly entail that the thickness of the outer shell of the particles in question is as small as possible. However, the requirement of a certain degree of mechanical rigidity of the particles dictates the lower limit to this thickness (as used within the context of the present invention, the term "mechanical rigidity" is not used merely in the sense of inflexibility alone, i.e. resistance to deformation, but is intended to imply inflexibility in combination with mechanical strength). The mechanical rigidity of the particles will also clearly be dependent on the ratio of the thickness of the outer shell to the external dimensions of the particles, and on the shape of the particles. In these respects, the optimum shape of the particles should clearly be spherical and the thickness of the outer shell should preferably be substantially uniform; a spherical shape will also normally be preferable with respect, for example, to the packing of such particles in chromatographic columns so as to achieve optimum flow of the fluid medium in question through the column.

Thus, in a preferred aspect of methods for the preparation of permeable hollow particles or permeable composite particles according to the invention, the ratio of the average thickness of the outer shell of the hollow particles used to the maximum linear separation between two points on the outer surface of the outer shell of the hollow particles is in the range $1/100-1/3$ for substantially all of the particles, preferably in the range $1/50-1/3$, more preferably in the range $1/30-1/5$, most preferably $1/20-1/10$. In a further preferred aspect of such methods, the outer surface of the outer shell of substantially all the hollow particles substantially defines a sphere, and in that case it is especially preferred that the outer shell of substantially all the hollow particles is of substantially uniform thickness.

As mentioned earlier, certain types of chromatographic procedures entail the use of rather high pressures; e.g. in the case of HPLC. hydrostatic pressures of 100 atm or more may be employed. For such applications it is clear that when permeable particles which are hollow to some extent are to be used as solid-phase carrier material, the particles must be able to withstand any difference which may arise (even though it may only be of short duration) between a higher external (e.g. hydrostatic) pressure and a lower internal (particle cavity) pressure. Thus, in another preferred aspect of the invention, when the hollow particles used in a method according to the invention are substantially spherical, the mechanical rigidity of the outer shell of the permeable hollow particles produced in the method is such that they are resistant to collapse and, substantially, to deformation at an external minus internal pressure differential of at least 0.1 atm, such as 1 atm, preferably at least 10 atm, more preferably at least 20 atm, most preferably at least 50 atm, especially at least 100 atm, particularly at least 200 atm.

In selecting hollow particles for use in a method according to the present invention, the material of the outer shell of the particles is thus clearly to be sought among certain types of natural or synthetic organic polymers, primarily synthetic organic polymers, and certain types of solid inorganic substances. Among types of synthetic organic polymers which may possibly be of interest are resins of the phenol-formaldehyde type and ABS resins, but other classes of synthetic organic polymers, such as polyamides, polyimides, polyesters, polyethers, polymeric vinyl compounds, polyalkenes and substituted derivatives thereof, as well as copolymers comprising more than one such said polymer functionality, and substituted derivatives of such copolymers, may well furnish suitable candidates. However, from the point of view of cheapness, ready availability and, as may be deduced from the earlier discussion above, formation of through-going pores, it is advantageous to employ hollow particles of inorganic material, especially since materials with the greatest mechanical rigidity are generally to be found amongst inorganic materials.

Thus, in a further aspect, the outer shell material, and thereby the porous material, of the hollow particles employed in methods for the preparation of permeable hollow particles or permeable composite particles according to the present invention comprises a member selected from the group consisting of solid inorganic compounds and non-metallic elements. In a preferred aspect, the latter material comprises a member selected from the group consisting of:

anhydrous forms of silicon dioxide, including amorphous silica and quartz, metal silicates, including silicates of lithium, sodium, potassium, calcium, magnesium, aluminium and iron, and metal borosilicates, such as borosilicates of said metals, metal phosphates, including hydroxyapatite, fluorapatite, phosphorite and autunite, metal oxides, including magnesium, aluminium, titanium, vanadium, chromium, manganese, iron, cobalt, nickel, copper, and silver oxides, solid non-metal oxides, including boric oxide, metal salts, including barium sulfate, and crystalline and amorphous forms of carbon, including graphite, carbon black and charcoal.

As explained earlier, the prior art discloses a number of examples of hollow, apparently substantially impermeable particles of siliceous glassy material which may be expected to be well suited as starting materials for use in a method for the preparation of permeable hollow particles or permeable composite particles according to the present invention, these previously disclosed particles being obtained relatively cheaply and straightforwardly either by deliberate synthesis or as a fly-ash by-product of certain combustion processes. Accordingly, in a further preferred aspect of the invention the material of the outer shell of the hollow particles employed in a method according to the invention, and thereby the porous material of the outer shell of the permeable hollow particles or permeable composite particles prepared. is a glass, preferably a synthetic glass comprising silicon dioxide and/or a silicate. In yet another preferred aspect of the invention, such an outer shell material is a silicon dioxide-containing material derived from fly-ash, in which case the material may be amorphous (e.g. glassy) or crystalline, or to some extent both amorphous and crystalline.

For certain applications of porous hollow or porous composite particles, it may be advantageous to be able to confine or retain the particles in question within a particular region of, for example, a process vessel or a chromatographic column, without the need for the incorporation of physical means of confinement or retention, such as a filter or some other form of boundary which permits contact between the particles and the medium with which they are to be brought into contact. The incorporation of an appropriate amount of a magnetic component, more specifically a paramagnetic component, in the outer shell material of the particles will render such confinement or retention possible by the application of a magnetic field of suitable strength. Furthermore, it will also be possible using, e.g., an electromagnetized probe, to collect together such particles, e.g. for the purpose of transferring them to another vessel for a treatment such as washing or the isolation of a particular chemical species bound on or within the particles. Thus, a further aspect of the invention provides methods for the preparation of permeable hollow particles or permeable composite particles in which the material, and thereby the porous material, of the outer shell of the hollow particles used comprises a paramagnetic component selected from the group consisting of:

paramagnetic metal oxides, including iron(II) oxide, iron (III) oxide, cobalt(II) oxide and nickel(II) oxide, and paramagnetic metal salts, including cobalt(II) salts, e.g. cobalt(II) phosphate, chromium(III) salts, e.g. chromium (III) fluoride, and manganese(II) salts, e.g. manganese(II) carbonate The majority of materials fall within two classes: (i) materials exhibiting only weak diamagnetism, and (ii) materials possessing net, relatively strong paramagnetism (including "permanently" magnetized ferromagnetic materials) deriving from the combined effect of a weak diamagnetic contribution and a relatively strong paramagnetic contribution. Paramagnetic materials useful as components in the context of the present invention are materials which fall within the latter category. Materials with only weak diamagnetism will generally be of little interest in the present context since the magnetic field strengths necessary to produce a useful degree of manipulative influence on particles comprising such a diamagnetic component in their outer shell will, in general, be prohibitively large.

Paramagnetic materials other than those mentioned above, examples being certain lanthanide compounds, such as compounds of dysprosium(III), erbium(III), gadolinium (III), holmium(III), samarium(III), terbium(III) or thulium (III), can also be envisaged as being of value, and the use of hollow particles comprising such materials in methods as herein described is intended to be be within the scope of the present invention.

As will be well known to a person skilled in the art, a number of the materials mentioned earlier, above, as constituents of the outer shell material of hollow particles used in methods according to the present invention are susceptible to chemical attack by acids and/or bases (acids and bases within the context of the present invention are so-called "Brønsted acids" and "Brønsted bases", i.e. substances which donate protons and accept protons, respectively). For example:

(i) Materials based on silicon dioxide, such as siliceous glassy materials, are generally susceptible to chemical attack by hydrofluoric acid and by certain bases, e.g. alkali metal hydroxides such as sodium hydroxide. Certain types of glass, e.g. certain types of borosilicate glass, may also be attacked by, e.g., hydrochloric or sulfuric acid.

(ii) Numerous metal oxides are chemically reactive towards acids and/or bases. For example, metal oxides such as magnesium oxide, copper(II) oxide and silver(I) oxide are basic in character, and they react with strong acids with the formation of salts, many of which are soluble in, e.g., aqueous media; on the other hand, metal oxides such as aluminium oxide and zinc oxide are amphoteric oxides, reacting both with strong acids and bases.

In GB 2141398 A, which relates to a method for making non-porous, hollow metal microspheres, there is very briefly mentioned the possibility of making microspheres porous to certain gases or liquids by incorporating, in the metal composition, a "specific metal" which can be selectively chemically leached from the metal microsphere, and as example is cited the possibility of selectively leaching copper from a copper and silver "metal glass" alloy using hydrochloric acid. No experimental results are provided to substantiate the proposed possibility; indeed, using an homogeneous metal alloy of the proposed type, it does not seem clear that through-going pore formation will take place without crumbling of the outer shell. Upon loss of the acid-leachable metal component from the alloy structure it seems likely that the cohesive integrity of the remaining metal will be lost, with attendant disintegration of the outer shell.

Quite apart from the above, porous hollow particles of metallic material will, if they can be prepared, be rather expensive to produce and will, in the case of many metals or alloys, be unsuited to many of the applications outlined in connection with the present invention (vide infra), e.g. when in contact with moderately acidic, basic or electrochemically aggressive media.

As mentioned earlier, the outer shell material of hollow particles within the context of the present invention may well be chemically and/or physically inhomogeneous. For example, it may, as demonstrated in the figures, below (vide infra), have a layered structure involving one or more layers of similar or different materials, e.g. various types of siliceous materials, and in such cases it may be necessary or advantageous to employ a succession of different reagents to bring about the formation of through-going pores. Alternatively, for example, it may consist of a siliceous material, such as a siliceous glassy material, containing particles or regions with a high content of a metal oxide which is reactive towards strong acids. In the latter case, treatment of the particles with, e.g., hydrochloric acid will, in many cases, lead to little, if any, attack on the siliceous matrix, but may lead to dissolution of the oxide component; depending on the content and distribution, in the outer shell material, of such oxide-containing particles or regions, the formation of through-going pores may thus be effected.

Other outer shell materials comprising inorganic and/or organic constituents, and which are locally or generally reactive towards acids and/or bases, thereby leading to the formation of through-going pores, can also be envisaged and are intended to be within the scope of the invention.

On the basis of the above discussion it is clear that the dissolution behaviour, notably towards acids and/or bases, of the outer shell materials of hollow particles employed in particularly preferred embodiments of methods according to the present invention, namely siliceous hollow particles of types already discussed, will be expected to be considerably different from that of metals and alloys, especially in view of the rather unforeseeable structural inhomogeneity or variability of the outer shell material of such particles, as illustrated by the figures and examples provided in the present specification (vide infra). It has, in fact, surprisingly been found, as demonstrated in the examples, that the degree of porosity produced in such siliceous hollow particles can be tailored to meet specific requirements by the judicious use of sequential treatments with various acidic or basic reagents.

Accordingly, in an aspect of the invention, one or more reagents used for treating the hollow particles employed in a method according to the invention comprise a substance selected from the group consisting of acids and bases, preferably a substance selected from the group consisting of hydrofluoric, hydrochloric, hydrobromic, hydriodic, nitric, sulfuric, perchloric, orthophosphoric, trifluoromethane-sulfonic and trifluoroacetic acids, and lithium hydroxide, sodium hydroxide, potassium hydroxide and calcium hydroxide. In further aspects of the invention, one or more of these reagents either comprises an aqueous acid selected from the group consisting of:

hydrofluoric acid of concentration 0.01–30M, preferably 1–25M. hydrochloric acid of concentration 0.01–13M, preferably 1–10M, orthophosphoric acid of concentration 0.01–18M, preferably 5–15M, nitric acid of concentration 0.01–22M, preferably 1–16M. or comprises an aqueous base selected from the group consisting of:

lithium hydroxide of concentration 0.01–4.5M, preferably 0.2–4M, sodium hydroxide of concentration 0.01–19M, preferably 0.2–5M, potassium hydroxide of concentration 0.01–14M, preferably 0.2–5M, calcium hydroxide of concentration 0.005–0.015M, preferably 0.01–0.015M.

Preferred embodiments of methods according to the invention for the preparation of permeable hollow particles or permeable composite particles employ siliceous, substantially spherical hollow particles as the starting material, and use strong inorganic acids and/or bases as the reagents for rendering the particles permeable. In one preferred aspect of the invention, the hollow particles employed are substantially spherical particles of siliceous glass, preferably soda-lime borosilicate glass, the size of substantially all of the particles being within the range of 1–5000 μm, suitably 1–4000 μm, advantageously 1–3000 μm, preferably 1–2000 μm, more preferably 1–1000 μm, most preferably 1–500 μm, such as 1–100 μm, including 5–85 μm, the average ratio of the thickness of the outer shell of the hollow particles to the outside diameter of the hollow particles being in the range 1/100–1/3 for substantially all of the particles, preferably in the range 1/50–1/3, more preferably in the range 1/30–1/5, most preferably 1/20–1/10, substantially all of the particles being initially impermeable, the reagent treatment of the hollow particles with one or more reagents so as to render them permeable by the formation of pores in the outer shell comprising subjecting, in any chosen order where relevant, including in the order given below, the substantially spherical hollow particles to one or more of the following treatments:

(a) aqueous sodium hydroxide in a concentration of 0.01–19M, preferably 0.2–5M, more preferably 0.2–1M, for a period of 0.5 hours–60 days, preferably 0.5 hours–30 days, more preferably 0.5–72 hours, most preferably 12–24 hours, at a temperature of ca. 20–ca. 110° C., preferably at the boiling point obtained under reflux conditions when open to the atmosphere, (b) aqueous hydrochloric acid in a concentration of 0.01–13M, preferably 1–10M, more preferably 1–5M, for a period of 0.5 hours–60 days, preferably 0.5 hours–30 days, more preferably 0.5–72 hours, most preferably 0.5–12 hours, especially 0.5–5 hours, at a temperature of ca. 20–ca. 110° C., preferably at the boiling point obtained under reflux conditions when open to the atmosphere, (c) aqueous hydrofluoric acid in a concentration of 0.01–30M, preferably 1–25M, more preferably 10–25M, for a period of 0.5–48 hours, preferably 1–24 hours, more preferably 1–18 hours, at a temperature of ca. 20–ca. 40° C., preferably at the temperature arising during the treatment when the treatment is initiated at ambient temperature, with the proviso that treatment (b) is not employed as the only treatment or as a first treatment.

In a further preferred aspect of the invention, the hollow particles employed are substantially spherical, optionally glassy, siliceous particles obtained as a component of the fly-ash formed upon combustion in a combustion plant, in an oxygen-containing gas, such as air, of a carbonaceous fuel containing inorganic chemical components appropriate for the formation of the fly-ash, the size of substantially all of the particles being within the range of 1–5000 μm, suitably 1–4000 μm, advantageously 1–3000 μm, preferably 1–2000 μm, more preferably 1–1000 μm, most preferably 1–500 μm, such as 1–100 μm, including 5–85 μm, the average ratio of the thickness of the outer shell of said hollow particles to the outside diameter of said hollow particles being in the range 1/100–1/3 for substantially all of the particles, preferably in the range 1/50–1/3, more preferably in the range 1/30–1/5, most preferably 1/20–1/10, substantially all of the particles being initially impermeable, said reagent treatment of the hollow particles with one or more reagents so as to render them permeable by the formation of pores in said outer shell comprising subjecting, in any chosen order where relevant, including in the order given below, the substantially spherical hollow particles to one or more of the following treatments:

(A) aqueous hydrochloric acid in a concentration of 0.01–13M, preferably 1–10M, more preferably 5–10M, for a period of 0.5 hours–60 days, preferably 0.5 hours–30 days, more preferably 5–72 hours, most preferably 12–24 hours, at a temperature of ca. 20–ca. 110° C., preferably at the boiling point obtained under reflux conditions when open to the atmosphere, (B) aqueous orthophosphoric acid in a concentration of 0.01–18M, preferably 5–15M, more preferably 10–15M, for a period of 0.5 hours–60 days, preferably 0.5 hours–30 days, more preferably 5–72 hours, most preferably 12–24 hours, at a temperature of ca. 20–ca. 160° C., preferably at the boiling point obtained under reflux conditions when open to the atmosphere, (C) aqueous hydrofluoric acid in a concentration of 0.01–30M, preferably 1–25M, more preferably 1–5M, for a period of 0.5–48 hours, preferably 12–24 hours, at a temperature of ca. 20–ca. 40° C., preferably at the temperature arising during the treatment when the treatment is initiated at ambient temperature, with the proviso that treatment (B) is not employed as the only treatment or as a first treatment.

If desired for some reason, it may thus be possible, using hollow particles within the latter two categories mentioned, to carry out treatments employing aqueous sodium hydroxide, aqueous hydrochloric acid or aqueous orthophosphoric acid without supplying heat but by allowing relatively long treatment times, e.g. of the order of several days, weeks or even months.

With regard to methods according to the invention employing hollow particles of fly-ash origin, if use is to be made of the resulting permeable hollow or permeable composite particles to prepare, purify or otherwise treat a preparation or substance which is to be employed in human or veterinary medicine or is intended for topical application to, or ingestion by, humans or animals, the objection might be raised that particles of fly-ash origin may possibly contain heavy metals, compounds thereof, or other undesirable species which could lead to contamination of the preparation or substance in question. If desired, this objection could, in principle, be overcome by providing, for example, an artificially prepared fuel comprising one or more well-defined combustible carbonaceous components together with siliceous and other inorganic chemical components, of specified chemical purity, appropriate for the formation of a suitable "fly-ash" upon combustion of the fuel in an oxygen-containing gas, such as air. It is presumed that combustion of such a fuel under essentially the same conditions as those for the combustion of those types of coal which give rise to the product known as "Fillite" (described earlier, above) will lead to the formation of a "fly-ash" containing siliceous hollow particles which are analogous to "Fillite" particles but which fulfil requirements with respect to the absence or low content of any undesirable species and which may [after collecting the "fly-ash", separating the particles in question from other "fly-ash" components, separating, if necessary, the impermeable hollow particles from any permeable particles which may be formed (e.g. by flotation in a liquid medium), and optionally fractionating the impermeable hollow particles into fractions of desired size intervals] then be used in a method according to the present invention.

Methods for the preparation of permeable composite particles can also be envisaged in which a second material is introduced into, or formed in situ within, certain types of siliceous hollow particles which initially possess through-going pores that have been formed during the formation of the particles themselves. For example, suitable particles might possibly be those disclosed, as discussed earlier, in U.S. Pat. No. 4,698,317; the latter include hollow, microspherical cordierite glass particles having "open pores", these particles being prepared by spray thermal decomposition of a solution, in an aqueous organic solvent such as an aqueous alcohol, containing a tetraalkyl silicate, an aluminium salt, a magnesium salt and, optionally, other compounds, the water content of the solution being adjusted so as to promote "open pore" formation. A second material could then be introduced into or formed within such particles in a manner as described in connection with methods according to the present invention.

Concerning the second material to be introduced into the particles in a method according to the invention for the preparation of permeable composite particles, this may, for example, be any type of material which is useful in connection with any of the previously mentioned applications of permeable composite particles prepared according to the invention. In one aspect of the invention this material comprises a member selected from the group consisting of solid inorganic compounds, metallic elements and alloys thereof, non-metallic elements, organic polymers of biological and synthetic origin, membrane-enclosed structures derived from biological cells, and virus particles. In a preferred aspect, the second material comprises a member selected from the group consisting of:

lipid vesicles,
virus particles, including attenuated and inactivated virus particles,
natural and synthetic polynucleotides and nucleic acids, including DNA, RNA, poly-A, poly-G, poly-U, poly-C and poly-T,
natural and synthetic polysaccharides and other carbohydrate-based polymers, including agaroses, celluloses, pectins, mucins, dextrans and starches,
natural and synthetic polypeptides and other amino acid based polymers, including albumins, hemoglobulins, immunoglobulins and enzymes,
synthetic organic polymers, including polyamides, polyimides, polyesters, polyethers, polymeric vinyl compounds, polyalkenes, and substituted derivatives thereof, as well as copolymers comprising more than one such organic polymer functionality, and substituted derivatives of such copolymers,
hydrated and anhydrous forms of silicon dioxide, including silica gel, amorphous silica and quartz,
metal silicates, including silicates of lithium, sodium, potassium, calcium, magnesium, aluminium and iron, and metal borosilicates, including borosilicates of said metals,
metal phosphates, including hydroxyapatite, fluorapatite, phosphorite and autunite,
metal oxides, including magnesium, aluminium, titanium, vanadium, chromium, manganese, iron, cobalt, nickel, copper, and silver oxides, and paramagnetic metal oxides, including iron(II), iron(III), cobalt(II) and nickel(II) oxides,
metal salts, including barium sulfate, and paramagnetic metal salts, including cobalt(II), chromium(III) and manganese(II) salts,
metallic elements, including magnesium, aluminium, titanium, vanadium, chromium, manganese, indium, copper, silver, gold, palladium, platinum, ruthenium, osmium, rhodium and iridium, and paramagnetic metallic elements, including iron, cobalt and nickel, and alloys of metallic and paramagnetic metallic elements, including alloys formed between said metallic and paramagnetic metallic elements.

Materials within several of the above categories, for example lipid vesicles, virus particles, certain polypeptides, and certain metal silicates and other metal salts, may be introduced into the cavities of permeable hollow particles in the form of solutions, suspensions or dispersions in suitable liquid media, after which the liquid medium is wholly or partly removed, for example by evaporation or freeze-drying.

Materials within some of the other categories, for example numerous polymers and copolymers, certain metal phosphates, certain metal oxides, e.g. silver oxide, and certain metallic elements, e.g. silver, may be introduced into the cavities of permeable hollow particles by forming them in situ via a series of steps involving the sequential introduction into the particles of a series of reagent solutions; for example, silver oxide might be deposited in situ within permeable hollow particles by partially infusing them with a aqueous solution of a soluble silver(I) salt, e.g. silver(I) nitrate, and then partially infusing them with an aqueous solution of a base, e.g. sodium hydroxide. The liquid solvent (s) may then be removed from the particles by, e.g., subjecting the particles to a vacuum treatment.

In some cases it may be possible to form a second material in situ within the permeable hollow particles by thermal treatment of a substance which has initially been introduced into or formed within the particles via the introduction of one or more solutions, suspensions or dispersions in liquid media, although this obviously will require that the outer shell material of the particles themselves suffers no detrimental effects as a result of the thermal treatment, for example, it is well known that the noble metals platinum and rhodium can be formed in finely divided, highly catalytically active form by heating almost any complex or binary compounds of the elements, e.g. $(NH_4)_2[PtCl6]$ or $(NH_4)_3[RhCl_6]$, at temperatures above about 200° C. in the presence of oxygen or air.

Using, for example, permeable hollow particles prepared from borosilicate glass, or other siliceous permeable hollow particles, such as "Fillite"-based particles, having a high softening temperature, it may thus be possible to prepare permeable composite particles with a content of noble metal; such particles may be useful, for example, for vapour-phase hydrogenation of unsaturated organic compounds.

For the use of permeable composite particles according to the invention in various chromatographic procedures, e.g. ion exchange chromatography, and in other procedures, for example solid-phase peptide synthesis, the particles in question may incorporate organic polymers or copolymers, notably synthetic polymers or copolymers. By way of example, the application of permeable composite particles according to the invention to peptide synthesis employing the classical chemical methodology of Merrifield [see, e.g., Baranv er al., Int. J. Peptide Protein Res. 30 (1987) pp. 705–739] will initially require the in situ formation of a cross-linked styrene/divinylbenzene copolymer resin by polymerization of styrene monomer containing, typically, about 1–2% of divinylbenzene; the resin may then be functionalized by subsequent treatment of the resin-containing composite particles with solutions of the appropriate reagents.

Thus, in a further aspect of a method according to the invention for the preparation of permeable composite particles, the second material comprises a polymer or a copolymer formed in situ within the permeable hollow particles by a procedure comprising the steps of:

immersing the permeable hollow particles in a solution, in a liquid solvent or solvent mixture, of one or more components which can polymerize or copolymerize to form a polymer or a copolymer or mixtures thereof, the solution optionally containing a polymerization catalyst or initiator, allowing the solution to at least partly fill the cavity within the permeable hollow particles via the through-going pores, allowing the polymer-/copolymer-forming components present in the solution within the hollow particles to polymerize/copolymerize to form solid polymer(s)/copolymer(s) therein, optionally substantially removing any liquid solution remaining within the cavity, optionally further treating the polymer-/copolymer-containing particles so as to:
  (i) at least partly chemically derivatize and/or modify the polymer(s)/copolymer(s) within the cavity therein and/or
  (ii) introduce further components into the cavity therein.

Materials other than those mentioned above may also conceivably be incorporated as components of porous composite particles; for example, for certain biotechnological applications, such as the preparation of vaccines, antibodies or toxins, or cell cultivation for the production of metabolites (e.g. the production of ethanol by yeast cells) it may be desirable, in a method according to the invention, to introduce live or dead cells of human, animal, plant, fungal or microorganism origin, or organelles (such as nuclei, mitochondria, chloroplasts or lysozomes) of similar origin, into porous hollow particles. This will, of course, necessitate the provision of relatively large permeable hollow particles having through-going pores of a suitably large size [e.g. of the order of ca. 5–20 $\mu$m in the case of several types of human cells, such as human erythrocytes (ca. 7 $\mu$m) and human liver cells (ca. 20 $\mu$m)], and it will then often be necessary or desirable, after the introduction of such cells or organelles, to coat the resulting particles by a suitable treatment, e.g. a treatment of the type mentioned earlier, above, so as to retain the cells or organelles within the particles but allow migration of smaller species into or out of the particles.

The optimum size or size-range of the through-going pores to be formed in a method according to the invention will, of course, vary very considerably, depending on the use to which the permeable hollow or permeable composite particles formed are to be put. Such pore sizes are difficult to characterize quantitatively; however, in terms of the size of the molecules which are to be capable of passing through the pores, a realistic upper exclusion limit for macromolecules, notably biological macromolecules, such as proteins, will often be a molecular weight of the order of magnitude of 108. The practical lower limit for pore size will generally be set by physico-chemical considerations, e.g. the detailed chemical structure of the outer shell and the manner in which the outer shell material dissolves or reacts during the pore-formation process. Although possibly rather difficult to achieve in a method according to the present invention, the formation of through-going pores with sizes of the order of a few Angstrom would be advantageous, in that the resulting permeable particles in question would be expected to be applicable as so-called "molecular sieves"; for example, a typical application of permeable hollow particles with pores of this size would be as materials for removing traces of water from organic solvents, and the relatively large internal cavity volume of such particles should confer a large drying capacity per particle.

The present invention further relates to permeable hollow particles and permeable composite particles prepared, respectively, by a method according to the invention for the preparation of permeable hollow particles and by a method according to the invention for the preparation of permeable composite particles.

The invention also relates co the use of permeable hollow particles according to the invention as a solid-phase matrix or substrate material in a procedure selected from the group consisting of:

chromatographic procedures, including HPLC., liquid chromatography, gas chromatography, ion-exchange, gel filtration, size-exclusion chromatography and affinity chromatography, filtration of a fluid medium, adsorption of at least one selected substance present in a fluid medium, absorption of at least one selected substance present in a fluid medium, heterogeneous catalysis of a reaction taking place in a fluid medium, immunochemical procedures, including immunosorption, solid-phase synthesis, including solid-phase peptide and protein synthesis, and solid-phase oligonucleotide synthesis, microbiological procedures, enzyme reactor procedures, carriage, on the outer surface of the particles, optionally after a suitable surface treatment, of live cells selected from cells of human, animal, plant, fungal and microorganism origin.

The term "fluid medium" as used in the context of the present invention means a liquid or gaseous medium.

In a further aspect, the present invention also relates to the use of permeable hollow particles prepared by a method according to the invention as the basis for a carrier for carrying, within the particles, a material selected from the one of the groups of second materials defined earlier, above.

A preferred aspect of the invention relates to the use of permeable composite particles according to the invention as a solid-phase matrix or substrate material in a procedure selected from the group consisting of:

chromatographic procedures, including HPLC., liquid chromatography, gas chromatography, ion-exchange, gel filtration, size-exclusion chromatography and affinity chromatography, immunochemical procedures, including immunosorption, solid-phase synthesis, including solid-phase peptide and protein synthesis, and solid-phase oligonucleotide synthesis, heterogeneous and homogeneous catalysis, microbiological procedures, enzyme reactor procedures, controlled release of a desired substance.

Examples of enzyme reactor procedures are:

(i) "confinement immobilization" procedures making use of an enzyme (e.g. in the form of an enzyme solution) which is contained within the through-going pores and/or the internal cavities of permeable particles, and which is prevented, as described earlier, above, from escaping from the particles by the presence of a suitable surface coating having diffusion or permeability characteristics such that the desired enzyme substrate(s) and resulting reaction product(s) may migrate through the coating;

(ii) "solid-phase covalent immobilization" procedures making use of an enzyme which is covalently bound, via appropriate functionalities, to the walls of the through-going pores and/or the internal cavities of permeable particles, or to a material deposited or contained within the latter pores and/or internal cavities, the resulting particles optionally being subjected to a surface treatment to provide a coating of the type mentioned in (i), above.

Such procedures might be employed, for example, in the production of high-fructose syrups from sucrose molasses, using permeable particles containing a suitable "confinement immobilized" or "solid-phase covalently immobilized" sucrase.

Controlled release (also known as sustained release, slow release or "retard" release) of a desired substance from particles will generally entail the presence of a suitable surface coating (e.g. a coating comprising a material chosen from the coating materials mentioned previously, above) having diffusion or permeability characteristics appropriate to the gradual release of the substance in question from the particles.

The present invention is further illustrated by reference to the examples given below and to FIGS. 1–4; the figures are electron microscopy photographs of treated and untreated "D32/4500" hollow, soda-lime borosilicate glass spheres (3M Corporation, USA), and are as follows:

FIG. 1 (magnification ×150) shows a sample of untreated particles as supplied. The bar near the top of the photograph represents 200 $\mu$m. The rather smooth surface and highly regular spherical form of these particles is clearly apparent.

Figure 2:
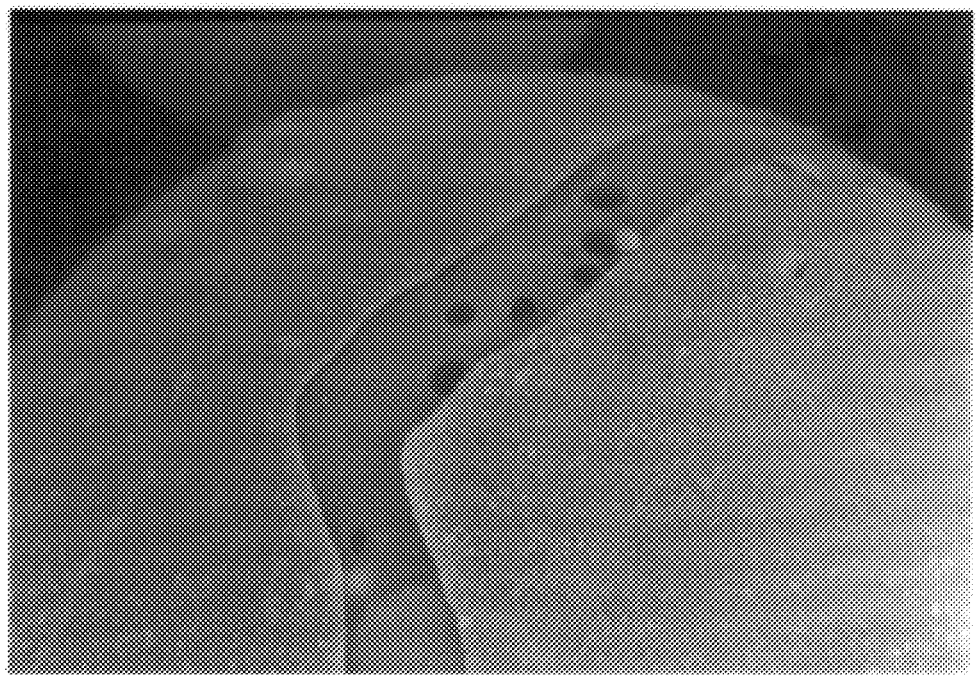
FIG. 2 (magnification ×200) shows a single particle present in a sample of particles which had been subjected, as described in Example 1(a).

FIG. 2 (magnification ×2000) shows a single particle present in a sample of particles which had been subjected, as described in Example 1(a) below, to treatment with aqueous 0.4M sodium hydroxide and then with aqueous 3M hydrochloric acid. The bar near the top of the photograph represents 20.0 $\mu$m. This particle appears to have a lavered structure. a number of relatively large, essentially circular craters in the underlying layer being visible.

Figure 3:
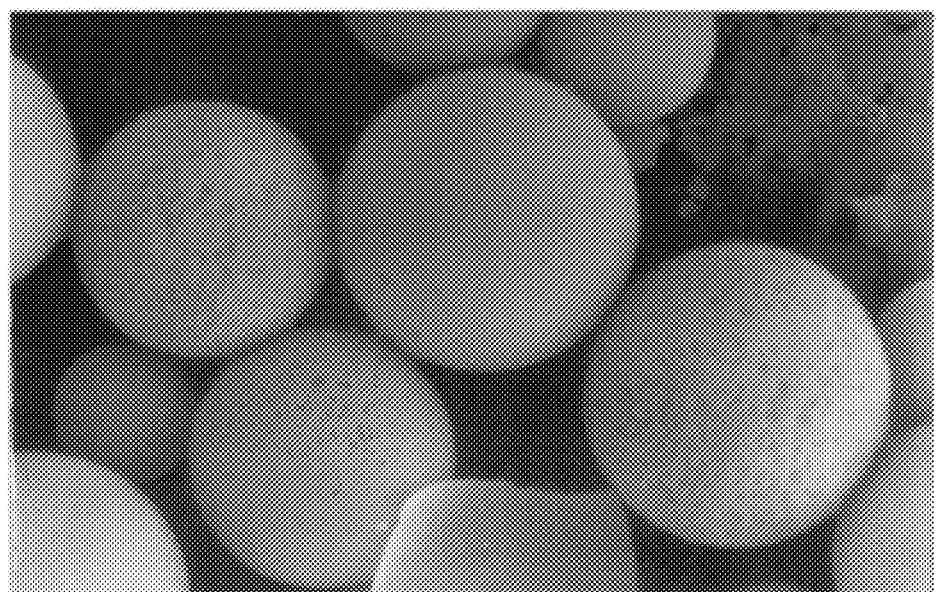
FIG. 3 (magnification ×2000) shows a sample of particles which had been subjected, as described in Example 1(b).

FIG. 3 (magnification ×2000) shows a sample of particles which had been subjected, as described in Example l(b) below, to treatment with aqueous 0.4M sodium hydroxide, then with aqueous 3M hydrochloric acid and finally with 38–40 % (w/w) hydrofluoric acid. The bar near the top of the photograph represents 20.0 $\mu$m. The highly cratered surface of some of the particles is clearly visible. The very thin fragment visible at bottom centre is probably the remains of a broken fragment of an outer layer of a particle (cf. FIG. 2).

Figure 4:
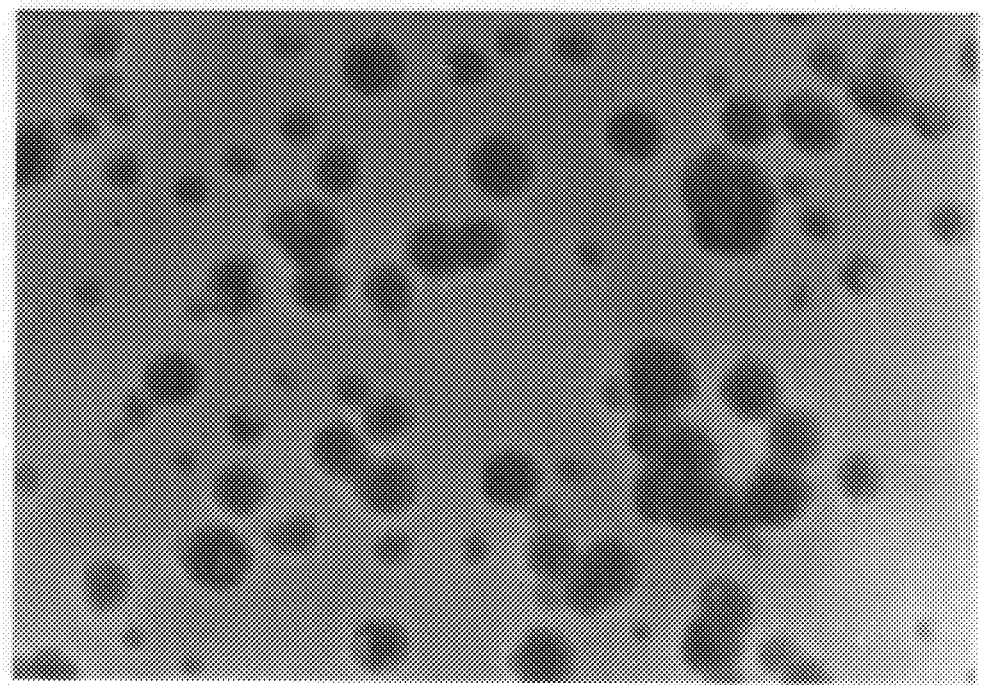
FIG. 4 (magnification ×20000) shows a ten-fold enlargement of the surface of the particle seen in the upper right-hand part of the lower left quadrant in FIG. 3.

FIG. 4 (magnification ×20000) shows a ten-fold enlargement of the surface of the particle seen in the upper right-hand part of the lower left quadrant in FIG.3. The bar near the top of the photograph represents 2.0 $\mu$m. The bottoms of some of the surface craters show clear evidence of the presence of further, smaller openings.

EXAMPLES

All solutions employed in the following examples are aqueous solutions unless otherwise indicated.

Example 1

Preparation of permeable hollow spheres from "D32/4500" hollow, soda-lime borosilicate glass spheres (3M Corporation, USA; according to the manufacturer, <3are retained on a 74 $\mu$m sieve).

(a) Preparation of particles exhibiting gel-filtration properties.

A 160 g portion of the above-mentioned hollow glass spheres was boiled under reflux for 24 h in 2 liters of 0.4M sodium hydroxide. The spheres were filtered off on a sintered glass filter, washed on the filter with 3–4 volumes of 0.01M sodium hydroxide and then boiled under reflux for 1–2 h in 1 liter of 3M hydrochloric acid. The spheres were then again isolated by filtration and washed thoroughly on the filter with distilled water, and they were then allowed to sediment from 5 liters of distilled water in order to remove the bulk of the fines. Decantation and discardment of the suspension of fines left ca. 150 ml of wet, permeable hollow spheres, of which $\geqq 99\%$ had a diameter of $\geqq 10$ $\mu$m.

Gel-filtration experiments.

Model experiments showed that the pore size of these spheres was suitable for gel-filtration of phenol from an aqueous solution containing phenol together with human serum proteins. However, the proteins exhibited a considerable degree of non-specific binding to the spheres, and for this reason the spheres were subjected to treatment with a 10% aqueous solution of 3-glycidoxypropyltrimethoxysilane (Janssen Chimica) at pH 3 and 90° C. for 2 h and then washed thoroughly with distilled water.

Spectrophotometric monitoring of the effluent from a column of the thus-treated permeable hollow spheres revealed excellent separation of phenol from the above-mentioned phenol/protein mixture.

(b) Preparation of particles permeable to phenol and protein molecules.

100 ml of moist, permeable hollow spheres prepared as described above under (a) [but not subjected to 3-glycidoxypropyltrimethoxysilane treatment] were stirred, without heating, in a polyethylene beaker for 1 h with 15 ml of 38–40 % (w/w) ($\equiv$ca. 22M) hydrofluoric acid. After isolation on a sintered glass filter and thorough washing on the filter with distilled water, the spheres were subjected to treatment with 3-glycidoxypropyltrimethoxysilane and washing as described above under (a).

Gel-filtration experiments.

Gel-filtration experiments showed that both the phenol and the human serum proteins in the above-mentioned phenol/protein solution were eluted from a column of the thus-treated spheres with a retention volume corresponding to 75–85% of the total column bed-volume, indicating permeability of these spheres towards both of these vastly different types of molecules.

Example 2

Preparation of permeable hollow spheres from "B46/4000" hollow, soda-lime borosilicate glass spheres (3M Corporation, USA).

200 g of the above-mentioned hollow glass spheres were stirred, without heating, for 18 h in a solution consisting of 1 liter of distilled water and 500 ml of 38–40% (w/w) hydrofluoric acid in a polyethylene beaker. After washing and sedimentation/decantation as described in Example l(a), the resulting spheres were isolated on a sintered glass filter and washed thoroughly with distilled water, giving ca. 150 ml of packed, moist spheres. The spheres were then subjected to treatment with 3-glycidoxypropyltrimethoxvsilane and washing as described in Example 1(a).

Gel-filtration experiments.

Gel-filtration experiments showed that the phenol and the proteins in the above-mentioned (Example 1) phenol/protein solution were eluted from a column of the thus-treated spheres with retention volumes corresponding to ca. 93% and ca. 85%, respectively, of the total column bed-volume, indicating permeability of these spheres towards both of types of molecules.

Example 3

Preparation of permeable hollow spheres from hollow spheres of siliceous material ("Fillite 75") derived from fly-ash (Fillite Ltd., Runcorn, England; particle size according to the manufacturer: 5–85

(a) Spheres treated with hydrochloric acid.

A 1 liter portion of "Fillite 75" was heated under reflux for 18 h in 1 liter of 30% (w/w) (≡ca. 9.5M) hydrochloric acid. After cooling to room temperature the spheres were isolated, washed and then subjected to sedimentation/decantation (from 5 liters of distilled water) as described in Example 1(a). The discarded fines amounted to ca. 5% (v/v) of the material.

Following this treatment the spheres were isolated on a sintered glass filter and washed with 10 volumes of distilled water.

(b) Spheres treated with hydrochloric acid+orthophosphoric acid.

Washed spheres prepared as in (a), above, were washed with one volume of 85% (w/w) (≡ca.14.7M) orthophosphoric acid on a sintered glassfilter and then heated under reflux for 18 h in 1 volume of 85% (w/w) orthophosphoric acid. After cooling to room temperature the spheres were isolated on a sintered glass filter and washed with 10 volumes of distilled water.

This treatment results in spheres which are much less coloured than after treatment (a), probably due to a reduction in the content of certain strongly-coloured metal species (e.g. iron silicates).

(c) Spheres treated with hydrochloric acid+orthophosphoric acid+hydrofluoric acid.

Washed spheres prepared as in (b), above, were stirred gently at ambient temperature for 18 h in 2 volumes of 5% (w/w) (≡ca. 2.5M) hydrofluoric acid in a polyethylene beaker. The spheres were then isolated on a sintered glass filter and washed thoroughly with distilled water.

Starting with 1 liter of "Fillite 75" and sequentially carrying out treatments (a), (b) and (c) as described above, the final yield of the moist, thus-treated spheres was ca. 600–700 ml.

Gel-filtration experiments.

To assess the degree of permeability of the spheres attained after the various treatments, columns were packed, respectively, with untreated spheres and spheres treated according to (a), (b) and (c) as described above, and gel-filtration experiments were performed using a test solution containing potassium dichromate, blue dextran and human serum proteins. The following results were obtained:

Untreated spheres: All the test components were eluted as one peak with a retention volume corresponding to ca. 30–40% of the total column bed-volume. This implies that the untreated spheres are essentially completely impermeable towards all three types of test solution components.

Spheres treated as in (a): The test components were eluted as two closely connected peaks with retention volumes corresponding to ca. 50–60% and 70–80%, respectively, of the total column bed-volume. Blue dextran was eluted in the first peak. This implies that treatment of spheres with hydrochloric acid renders them partially permeable towards species of high molecular weight and considerably more permeable towards species of low molecular weight.

Spheres created as in (b): The results obtained were essentially the same as for spheres treated with hydrochloric acid as in (a).

Spheres treated as in (c): All the test components were eluted as one peak with a retention volume corresponding to ca. 80–95% of the total column bed-volume. This implies that the spheres after this treatment are completely permeable towards species with a molecular weight up to ca. $2 \times 10^6$, or possibly higher.

Flow capacity experiments.

The flow capacity of spheres treated as in (c), above, was examined using a 10 mm i.d.×10 cm long packed column. A flow rate of 20 ml/min (the maximum obtainable with the experimental set-up employed) did not cause the column to collapse. The hydrostatic back-pressure at 20 ml/min was between ca. 10 and 20 atm (i.e. between ca. 1 and 2 MPa).

Example 4

Preparation of permeable composite "Fillite 75"-based spheres containing polymerized acrylamide/bisacrylamide.

(a) Preparation by polymerization "en masse".

A 100 ml portion of packed, moist spheres treated with hydrochloric acid, orthophosphoric acid and hydrofluoric acid as described in Example 3(c) was washed, on a sintered glass-filter, with 250 ml of an aqueous solution containing 4% (w/v) of acrylamide, 4% (w/v) of bisacrylamide, 0.5% (w/v) of ammonium persulfate and 20% (v/v) of ethanol. The mixture was then drained and the resulting mushy mass was transferred to a beaker.

250 $\mu$l of N,N',N'',N'''-tetramethylethylenediamine (TMEDA) was added to the mass with thorough stirring. After a few minutes the material thickened considerably in consistency, indicating the onset of polymerization. The material was then left without stirring for 1 h to ensure completion of polymerization, after which the resulting "soft cake" was mashed carefully to a homogeneous mass having a porridge-like consistency (this mashing procedure facilitates subsequent removal of externally adhering monomer/polymer material) and then suspended in distilled water. The spheres were washed thoroughly by several sedimentation/decantation cycles using distilled water.

Using varying concentrations of acrylamide/bisacrylamide in the solution used to "wash" the permeable hollow spheres, the same procedure was employed to prepare permeable composite spheres containing gels having other concentrations of polymerized acrylamide/bisacrylamide Gel-filtration experiments In gel-filtration experiments performed as described in Example 3, no difference between the behaviour of permeable, polymer-containing spheres and that of permeable hollow spheres prepared as in Example 3(c) was seen when the total concentration of acrylamide and bisacrylamide in the solution used to "wash" the permeable hollow spheres was below ca. 5% (w/v); however, upon increasing the concentration of the monomers, and thereby increasing the relative content of polymer within the spheres, the permeability of the resulting spheres towards blue dextran and human serum proteins was found to be gradually reduced.

There is thus the possibility of "tailoring" spheres of this type as necessary to suit particular gel-filtration tasks.

Flow capacity experiments.

Experiments performed as described in Example 3 using spheres prepared as in (a), above, with a variety of gel polymer concentrations showed that the flow capacity of these spheres was still higher than 20 ml/min. The hydrostatic back-pressure was found in general to be slightly higher than for the hollow spheres, viz. ca. 20 atm (i.e. ca 2MPa) at 20 ml/min.

(b) Preparation by polymerization in suspension.

A 100 ml portion of packed, moist spheres treated with hydrochloric acid, orthophosphoric acid and hydrofluoric acid as described in Example 3(c) was washed, on a sintered glass-filter, with 250 ml of a 0.2M potassium phosphate solution (pH 6.0) containing 4% (w/v) of acrylamide, 4% (w/v) of bisacrylamide, 0.5% (w/v) of ammonium persulfate and 20% (v/v) of ethanol. The mixture was then drained and the resulting mushy mass was transferred to a beaker containing 1 liter of grape seed oil and 10 ml of "Cremophor" (a commercially available emulsifying agent; BASF). 10 ml of TMEDA was added with stirring, and the mixture was then stirred for 1 h with a paddle-stirrer operating at 500 rpm. The resulting suspension was poured into 5 liters of distilled water. The spheres were washed several times by sedimentation/decantation from distilled water and finally collected on a sintered glass-filter and washed thoroughly with distilled water.

Gel-filtration experiments and flow capacity experiments gave results comparable to those described in (a), above.

Example 5

Preparation of permeable composite "Fillite 75"-based spheres containing a copolymer of acrylamide and allyl-agarose, and subsequent functionalization with vinyl sulfone groups.

The above copolymeric material was formed in situ within permeable hollow spheres in a manner analogous to that described in Example 4(a), using 100 ml of spheres and 250 ml of an aqueous solution containing 2% (w/v) of acrylamide, 2% (w/v) of "Acryl Aide" (an allyl-agarose derivative obtained from FMC Marine Colloids, USA) and 0.5% (w/v) of ammonium persulfate.

The resulting spheres were allowed to react for 1 h with 100 ml of a 1% (v/v) solution of divinyl sulfone in 0.5M potassium phosphate (pH 11), and then washed extensively with water.

Preliminary experiments showed that the thus-treated spheres, now containing vinyl sulfone groups coupled to the copolymer substrate, were capable of covalently immobilizing proteins and other species containing nucleophilic groups.

We claim:

1. A method for the preparation of permeable hollow particles having an outer shell of a mechanically rigid porous material, the size of the particles being within the range from 1 µm to 5000 µm, the method comprising:
   (a) taking impermeable, substantially spherical, hollow, particles having an outer shell of a mechanically rigid material, the outer shell comprising a member selected from the group consisting of anhydrous forms of silicon dioxide, metal silicates, metal borosilicates, metal oxides, and boric oxide, the size of the particles being within the range from 1 µm to 5000 µm, and
   (b) treating said hollow particles with one or more reagents selected from the group consisting of acids and bases capable of rendering said hollow particles permeable by the formation of through-going pores in the outer shell by chemical reaction or solvent/solute dissolution so as to form substantially spherical permeable hollow particles having a cavity defined by the inner surface of the outer shell, said cavity being connected with the surroundings by the through-going pores, the permeability of said particles being such as to permit chemical species to traverse their outer shell via said through-going pores, wherein step (b) is carried out at a temperature of about 20° C. to the boiling point of said acid or base obtained under reflux conditions open to the atmosphere;

with a first proviso that, if step (b) includes treatment with hydrochloric acid, then said treatment is not employed as the only treatment or as an initial treatment when said particles of step (a) are soda-lime borosilicate glass, and with a second proviso that, if step (b) includes treatment with orthophosphoric acid, then said treatment is not employed as the only treatment or as an initial treatment when said particles of step (a) are siliceous particles obtained as a component of the fly-ash formed upon combustion in a combustion plant, and with a third proviso that said mechanically rigid material is not a material selected from metal and alloys thereof.

2. A method according to claim 1 and comprising a further step of subjecting the resulting permeable hollow particles to a surface treatment so as to modify the physical or chemical properties of the outer and inner surface of said outer shell.

3. A method according to claim 1, the size of said hollow particles, and thereby of said prepared permeable hollow particles, being within the range of 1–500 µm.

4. A method according to claim 1, the ratio of the average thickness of said outer shell of said hollow particles to the maximum linear separation between two points on the outer surface of said outer shell of said hollow particles being in the range 1/30–1/5.

5. A method according to claim 1, the outer shell of said hollow particles being of substantially uniform thickness.

6. A method according to claim 1, the mechanical rigidity of the outer shell of said permeable hollow particles being such that they are resistant to collapse and deformation at an external minus internal pressure differential of at least 10 atm.

7. A method according to claim 1, said outer shell material, and thereby said outer shell containing said pores, comprising a member selected from the group consisting of: amorphous silica, quartz lithium silicate, sodium silicate, potassium silicate, calcium silicate, magnesium silicate, aluminium silicate, iron silicate, lithium borosilicate, sodium borosilicate, potassium borosilicate, calcium borosilicate, magnesium borosilicate, aluminium borosilicate, and iron borosilicate, magnesium oxide, aluminium oxide, titanium oxide, vanadium oxide, chromium oxide, manganese oxide, iron oxide, cobalt oxide, nickel oxide, copper oxide, silver oxides, and boric oxide.

8. A method according to claim 1, said outer shell material being a glass comprising silicon dioxide or a silicate.

9. A method according to claim 1, said outer shell material being a silicon dioxide-containing material derived from fly-ash.

10. A method according to claim 1, wherein one or more of said reagents used for treating said hollow particles comprises a substance selected from the group consisting of hydrofluoric acid, hydrochloric acid, hydrobromic acid, hydroiodic acid, nitric acid, sulfuric acid, perchloric acid, orthophosphoric acid, trifluoromethanesulfonic acid, trifluoroacetic acid lithium hydroxide, sodium hydroxide, potassium hydroxide and calcium hydroxide.

11. A method according to claim 1, one or more said reagents used for treating said hollow particles comprising an aqueous acid selected from the group consisting of: hydrofluoric acid of concentration 0.01–30M, hydrochloric acid of concentration 0.01–13M, orthophosphoric acid of concentration 0.01–18M, and nitric acid of concentration 0.01–22M.

12. A method according to claim 11, one or more said reagents used for treating said hollow particles comprising an aqueous acid selected from the group consisting of: hydrofluoric acid of concentration 1–25M, hydrochloric acid of concentration 1–10M, orthophosphoric acid of concentration 5–15M, and nitric acid of concentration 1–16M.

13. A method according to claim 1, one or more said reagents used for treating said hollow particles comprising an aqueous base selected from the group consisting of: lithium hydroxide of concentration 0.01–4.5M, sodium hydroxide of concentration 0.01–19M, potassium hydroxide of concentration 0.01–14M, and calcium hydroxide of concentration 0.005–0.015M.

14. A method according to claim 13, one or more said reagents used for treating said hollow particles comprising an aqueous base selected from the group consisting of: lithium hydroxide of concentration 0.2–4M, sodium hydroxide of concentration 0.2–5M, potassium hydroxide of concentration 0.2–5 M, and calcium hydroxide of concentration 0.01–0.015M.

15. A method according to claim 8, said hollow particles being impermeable substantially spherical particles of siliceous glass, the size of the particles being within the range of 1–500 $\mu$m, the average ratio of the thickness of the outer shell of said hollow particles to the outside diameter of said hollow particles being in the range $1/30$–$1/5$, said reagent treatment of the hollow particles with one or more reagents so as to render them permeable by the formation of pores in said outer shell comprising subjecting, in any chosen order said substantially spherical hollow particles to one or more treatments selected from the group consisting of:
   (a) aqueous sodium hydroxide in a concentration of 0.2–5M for a period of 0.5–72 hours at a temperature in the range of 20°–110° C.,
   (b) aqueous hydrochloric acid in a concentration of 1–10M for a period of 0.5–72 hours at a temperature in the range of 20°–110° C., and
   (c) aqueous hydrofluoric acid in a concentration of 1–25M for a period of 0.5–48 hours at a temperature in the range of 20°–40° C.,
with the proviso that treatment (b) is not employed as the only treatment or as a first treatment.

16. A method according to claim 1, said hollow particles being impermeable substantially spherical siliceous particles obtained as a component of the fly-ash formed upon combustion in a combustion plant, in an oxygen-containing gas of a carbonaceous fuel containing inorganic chemical components the size of the particles being within the range of 1–500 $\mu$m the average ratio of the thickness of the outer shell of said hollow particles to the outside diameter of said hollow particles being in the range $1/30$–$1/5$, the particles being initially impermeable, said reagent treatment of the hollow particles with one or more reagents so as to render them permeable by the formation of pores in said outer shell comprising subjecting, in any chosen order said substantially spherical hollow particles to one or more treatments selected from the group consisting of:
   (a) aqueous hydrochloric acid in a concentration of 1–10M for a period of 5–72 hours at a temperature in the range of 20°–110 C.,
   (b) aqueous orthophosphoric acid in a concentration of 5–15M for a period of 5–72 hours at a temperature in the range of 20°–160° C., and
   (c) aqueous hydrofluoric acid in a concentration of 1–5M, for a period of 0.5–48 hours at a temperature in the range of 20°–40° C., with the proviso that treatment (b) is not employed
as the only treatment or as a first treatment.

17. Permeable hollow particles prepared by a method for the preparation of permeable hollow particles according to claim 1.

18. A permeable particle as claimed in claim 17, wherein said particle comprises an immobilized enzyme or a cell.

19. A method for the preparation of permeable composite particles having an outer shell of a mechanically rigid porous first material, the size of the particles being within the range from 1 $\mu$m to 5000 $\mu$m, the inner surface of said outer shell defining a cavity in which is contained a second material, said second material comprising a homopolymer or a copolymer formed in situ within said permeable hollow particles, the method comprising:
   (a) taking impermeable, substantially spherical impermeable hollow particles having an outer shell of a mechanically rigid material and a cavity defined by the inner surface of said outer shell, the outer shell comprising a member selected from the group consisting of anhydrous forms of silicon dioxide, metal silicates, metal borosilicates, metal oxides, and boric oxide, the size of the particles being within the range from 1 $\mu$m to 5000 $\mu$m, and
   (b) treating said hollow particles with one or more reagents selected from the group consisting of acids and bases capable of rendering said hollow particles permeable by the formation of through-going pores in the outer shell by chemical reaction or solvent/solute dissolution so as to form substantially spherical permeable hollow particles having a cavity defined by the inner surface of the outer shell, said cavity being connected with the surroundings by the through-going pores, the permeability of said particles being such as to permit chemical species to traverse their outer shell via said through-going pores,
   (c) immersing said permeable hollow particles in a solution, in a liquid solvent, of one or more components which can polymerize to form a homopolymer or a copolymer, said solution optionally containing a polymerization catalyst or initiator,
   (d) allowing said solution to at least partly fill said cavity within said permeable hollow particles via said through-going pores, and
   (e) allowing said homopolymer-/copolymer-forming components present in the solution within said hollow particles to polymerize to form solid homopolymer(s)/copolymer(s) therein;
with a first proviso that if step (b) includes treatment with hydrochloric acid, then said treatment is not employed as the only treatment or as an initial treatment when said particles of step (a) are soda-lime borosilicate glass,
and with a second proviso if step (b) includes treatment with orthophosphoric acid, then said treatment is not employed as the only treatment or as an initial treatment when said particles of step (a) are siliceous particles obtained as a component of the fly-ash formed upon combustion in a combustion plant, and
with a third proviso that said mechanically rigid material is not a material selected from metal and alloys thereof.

20. Permeable composite particles prepared by a method for the preparation of permeable composite particles according to claim 19.

21. A permeable particle as claimed in claim 20, wherein said particle comprises an immobilized enzyme or a cell.

* * * * *

UNITED STATES PATENT AND TRADEMARK OFFICE
CERTIFICATE OF CORRECTION

PATENT NO. : 5,770,416
DATED : June 23, 1997
INVENTOR(S) : Allan O.F. LIHME et al.

It is certified that error appears in the above-identified patent and that said Letters Patent is hereby corrected as shown below:

Column 24, line 35,

Claim 7, after quartz and before lithium insert -- , --.
Column 25, line 45, Claim 16, after 1-500 um and before the insert -- , --.

Signed and Sealed this

Twenty-sixth Day of January, 1999

Attest:

Attesting Officer

Acting Commissioner of Patents and Trademarks